(12) United States Patent
Smaardijk et al.

(10) Patent No.: US 8,802,900 B2
(45) Date of Patent: *Aug. 12, 2014

(54) PROCESS FOR THE PREPARATION OF ETHYLENE GLYCOL

(75) Inventors: Abraham Adriaan Smaardijk, Amsterdam (NL); Jacqueline Hessing, legal representative, Castricum (NL); Hendrik Stichter, Amsterdam (NL)

(73) Assignee: Shell Oil Company, Houston, TX (US)

( * ) Notice: Subject to any disclaimer, the term of this patent is extended or adjusted under 35 U.S.C. 154(b) by 285 days.

This patent is subject to a terminal disclaimer.

(21) Appl. No.: 13/302,682

(22) Filed: Nov. 22, 2011

(65) Prior Publication Data

US 2012/0136178 A1 May 31, 2012

(30) Foreign Application Priority Data

Nov. 29, 2010 (EP) ..................................... 10193003

(51) Int. Cl.
*C07C 27/02* (2006.01)

(52) U.S. Cl.
USPC ............................. 568/858; 568/852; 568/857

(58) Field of Classification Search
None
See application file for complete search history.

(56) References Cited

U.S. PATENT DOCUMENTS 4,400,559 A    8/1983  Bhise ............................ 568/858

*Primary Examiner* — Sudhakar Katakam

(57) ABSTRACT

The invention provides a process for the production of ethylene glycol from ethylene. An ethylene glycol stream comprises inorganic chloride contaminants and the process comprises steps of converting the inorganic chloride contaminants to 2-chloroethanol by reaction with ethylene oxide in one or more dehydration columns, and removing 2-chloroethanol in a waste water stream.

10 Claims, 2 Drawing Sheets

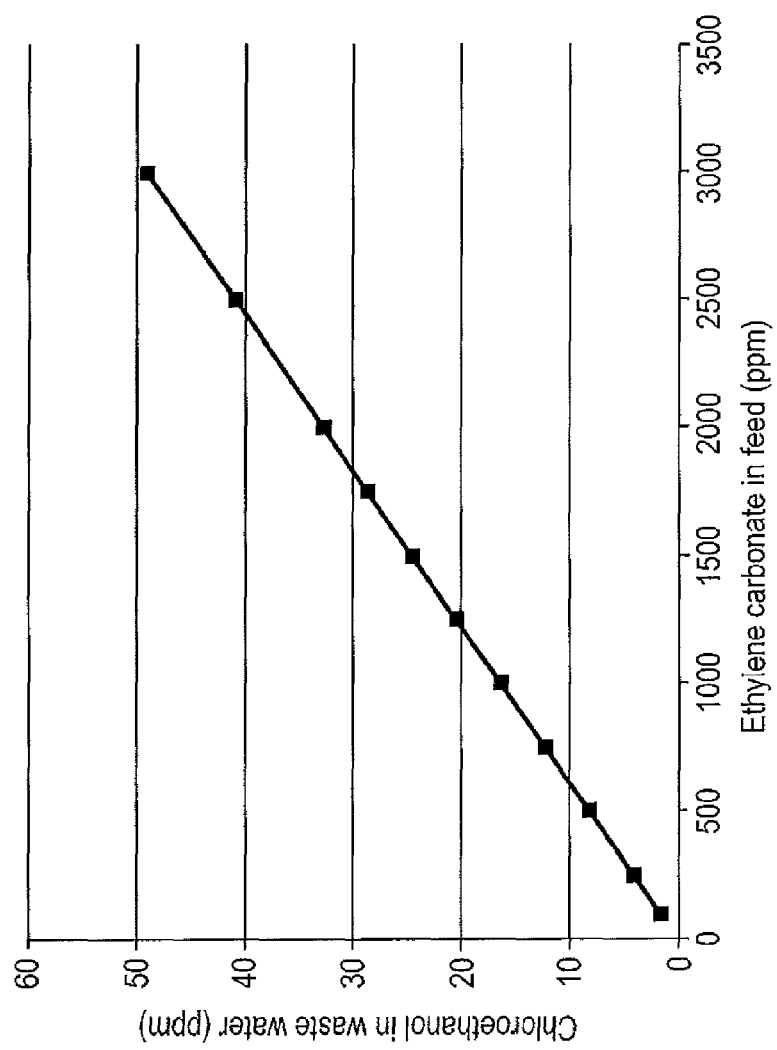

PROCESS FOR THE PREPARATION OF ETHYLENE GLYCOL

This application claims the benefit of European Application No. 10193003.0 filed Nov. 29, 2010, which is incorporated herein by reference.

FIELD OF THE INVENTION

The present invention relates to a process for the preparation of an ethylene glycol from ethylene.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide, which is in turn prepared from ethylene. In order to produce ethylene oxide, ethylene and oxygen are passed over an epoxidation catalyst, for example, a silver oxide catalyst, typically at pressures of 10-30 bar and temperatures of 200-300° C., producing a product stream comprising ethylene oxide, carbon dioxide, ethylene, oxygen and water. The amount of ethylene oxide in the product stream is usually between about 0.5 and 10 weight percent. The product stream is supplied to an ethylene oxide absorber and the ethylene oxide is absorbed by a recirculating solvent (absorbent) stream containing mostly water. After absorption, the aqueous ethylene oxide stream is sent to a stripper in order to separate the ethylene oxide. The ethylene oxide leaves the top of the stripper as a concentrated aqueous ethylene oxide stream.

In one well-known process, ethylene oxide is then catalytically reacted with carbon dioxide to produce ethylene carbonate. The ethylene carbonate is subsequently hydrolysed to provide ethylene glycol. Reaction via ethylene carbonate significantly improves the selectivity of ethylene oxide conversion to monoethylene glycol compared to the known process wherein ethylene oxide is reacted with a large excess of water to form ethylene glycol in a non-catalytic process.

The catalytic reaction of ethylene to ethylene oxide usually takes place in the presence of a moderator, which controls the performance of the epoxidation catalyst. Commonly used moderators include monochloroethane or dichloroethane. The use of these organic chloride moderators leads to the presence of organic chloride contaminants in the ethylene oxide product stream that is supplied to the ethylene oxide absorber. These organic chloride contaminants are absorbed in the ethylene oxide absorber, are present in the stream supplied to the ethylene oxide stripper and are present in the concentrated aqueous ethylene oxide stream taken from the top of the ethylene oxide stripper.

If the ethylene oxide is catalytically converted to monoethylene glycol via ethylene carbonate, the presence of the organic chloride contaminants in the concentrated ethylene oxide stream can lead to problems. The organic chloride contaminants can react with hydrolysis catalysts such as potassium carbonate to produce inorganic chloride contaminants (e.g. potassium chloride). Therefore, the contaminants can cause degradation of the hydrolysis catalysts and can also lead to a build-up of inorganic chloride. The inorganic chloride can start to precipitate and may cause chloride stress corrosion.

To avoid build-up of inorganic chloride it is usual to remove a portion of the catalyst via a catalyst bleed in the catalyst recycle loop (and thereby also remove inorganic chloride contaminants). So that expensive catalyst is not lost, it is also usual to recover catalyst from the catalyst bleed so that it can be reused. This is a relatively expensive process, so it is desirable to limit the quantity of catalyst bleed.

The present inventors have sought to provide an improved process wherein the requirement for a catalyst bleed is reduced.

SUMMARY OF THE INVENTION

Surprisingly the present inventors have found that inorganic chloride contaminants can be converted to 2-chloroethanol in the dehydrator section of an ethylene glycol plant, and this 2-chloroethanol is removed with the waste water. This reduces or removes the need for a catalyst bleed.

Accordingly, the present invention provides a process for the production of ethylene glycol from ethylene, said process comprising the steps of:
 i) converting ethylene in the presence of oxygen, an epoxidation catalyst and a moderator to ethylene oxide in an ethylene oxide reactor;
 ii) absorbing the ethylene oxide in an aqueous absorbent and then stripping said absorbent to provide an aqueous ethylene oxide stream;
 iii) converting the aqueous ethylene oxide stream in the presence of one or more catalysts and carbon dioxide to an ethylene carbonate stream in one or more carboxylation reactors;
 iv) converting the ethylene carbonate stream in the presence of one or more catalysts to a first ethylene glycol stream in one or more hydrolysis reactors;
 v) removing water from the first ethylene glycol stream to form a dehydrated ethylene glycol stream and a waste water stream in one or more dehydration columns;
 vi) purifying the dehydrated ethylene glycol stream in one or more glycol distillation columns to form a purified ethylene glycol product stream and a catalyst recycle stream;
wherein the first ethylene glycol stream comprises inorganic chloride contaminants and wherein the process comprises the additional steps of
 vii) converting the inorganic chloride contaminants to 2-chloroethanol by reaction with ethylene oxide in the one or more dehydration columns; and
 viii) removing 2-chloroethanol in the waste water stream.

BRIEF DESCRIPTION OF THE DRAWINGS

FIG. 2 is a graph depicting a prediction of how chloroethanol in waste water varies as a function of the ethylene carbonate level in the first ethylene glycol stream.

DETAILED DESCRIPTION OF THE INVENTION

Figure 1:
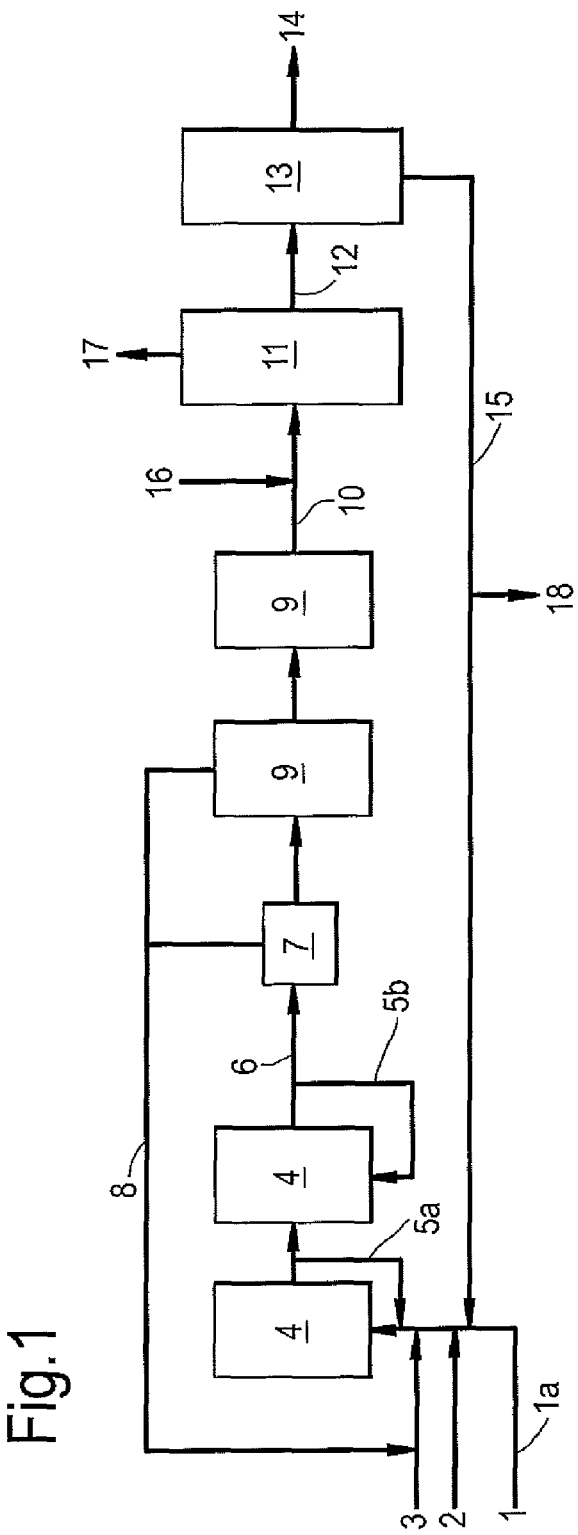
FIG. 1 is a schematic diagram showing a process according to an embodiment of the invention.

The ethylene is reacted with oxygen in the presence of an epoxidation catalyst in a reactor to produce a gas composition comprising ethylene oxide, ethylene, oxygen, carbon dioxide and water vapour. The oxygen may be supplied as oxygen or as air, but is preferably supplied as oxygen. Ballast gas, for example methane or nitrogen, is typically supplied to allow operation at high oxygen levels without causing a flammable mixture. A moderator, e.g. monochloroethane, dichloroethane or vinyl chloride, is supplied for catalyst performance control. The moderator is suitably an organic chloride compound. The ethylene, oxygen, ballast gas and moderator are preferably supplied to recycle gas that is supplied to the ethylene oxide reactor from the ethylene oxide absorber (optionally via a carbon dioxide absorption column).

The ethylene oxide reactor is typically a multitubular, fixed bed reactor. The epoxidation catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C. The gas composition from the ethylene oxide reactor is preferably cooled in one or more coolers, preferably with generation of steam at one or more temperature levels.

Contaminants are preferably removed from the gas composition before it is supplied to the ethylene oxide absorber. Possible contaminants include acids, esters, aldehydes, acetals and organic halides. A preferred method of removing contaminants is quenching, preferably by contacting the gas composition with a cooled recirculating aqueous solution. Despite such a step, the gas composition supplied to the ethylene oxide absorber will contain organic chloride contaminants originating from the moderator used in the catalytic oxidation reaction.

The gas composition from the oxidation step is then supplied to an ethylene oxide absorber preferably comprising a column of vertically stacked trays or comprising a packed column.

Aqueous absorbent is supplied to the ethylene oxide absorber and is contacted with the gas composition in the ethylene oxide absorber. Typically the absorbent supplied to the ethylene oxide absorber is known as lean absorbent, and the stream leaving the ethylene oxide absorber (having absorbed ethylene oxide, carbon dioxide and light ends) is known as fat absorbent.

The lean absorbent suitably comprises at least 50 wt % water. Preferably, the lean absorbent comprises at least 80 wt % water.

The fat absorbent withdrawn from the absorber is supplied to a stripper. An aqueous ethylene oxide stream is produced from the top of the stripper. The remaining absorbent, now lean absorbent, is recycled to the ethylene oxide absorber.

The aqueous ethylene oxide stream from the top of the stripper suitably contains at least 50 wt % ethylene oxide, preferably at least 55 wt %. In certain embodiments, a stripper-concentrator is used, wherein the top product from the stripper is further concentrated. In these embodiments, the aqueous ethylene oxide stream may contain at least 95 wt % ethylene oxide. In these embodiments, the aqueous ethylene oxide stream is diluted with water before being provided to the ethylene oxide to ethylene glycol section of the process.

The aqueous ethylene oxide stream is then provided to the ethylene oxide to ethylene glycol section of the process and is supplied to one or more carboxylation reactors. Carbon dioxide and a catalyst stream are also provided. The carbon dioxide and catalyst streams may be provided to the carboxylation reactor(s) separately from the aqueous ethylene oxide stream. Preferably, the carbon dioxide and catalyst streams are combined with the aqueous ethylene oxide stream prior to the aqueous ethylene oxide stream being supplied to the carboxylation reactor(s).

The catalyst stream comprises one or more catalysts that promote carboxylation and hydrolysis. If only one catalyst is present, then the catalyst must promote carboxylation and hydrolysis. If two or more catalysts are present, then each catalyst can promote carboxylation or hydrolysis or can promote both reactions (provided that at least one catalyst promotes carboxylation and at least one catalyst promotes hydrolysis).

In the present invention, the one or more catalysts that promote carboxylation and hydrolysis is/are homogeneous. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Homogeneous catalysts that are known to promote hydrolysis include basic alkali metal salts such as potassium carbonate, potassium hydroxide and potassium bicarbonate, or alkali metal metalates such as potassium molybdate. Preferred homogeneous catalyst systems include a combination of potassium iodide and potassium carbonate, and a combination of tributylmethylphosphonium iodide and potassium carbonate.

The catalyst stream is supplied to the carboxylation reactor either separately or after mixing with the aqueous ethylene oxide and/or $CO_2$ streams. After carboxylation, hydrolysis and dehydration, it is separated from the product stream in the catalyst separation section of the glycol distillation column. As the process of the present invention proceeds, a catalyst recycle stream from the catalyst separation section will be recycled to the carboxylation step.

Carboxylation of the aqueous ethylene oxide stream in the presence of carbon dioxide to produce an ethylene carbonate stream occurs in one or more carboxylation reactors. If more than one reactor is present, they are preferably arranged in series.

The carboxylation reactors are suitably two-phase flow reactors operating at a pressure in the range of from 0.8 to 3.0 MPa and a temperature in the range of from 50 to 180° C.

The carboxylation reactors will preferably each be provided with a liquid recycle wherein liquid is removed from the reactor and then recycled to the bottom of the reactor. The recycle stream can be heated or cooled in order to provide improved temperature control to the carboxylation reactor.

Some hydrolysis will have occurred in the carboxylation reactors such that the ethylene carbonate stream will comprise some ethylene glycol.

After the aqueous ethylene oxide stream is converted to an ethylene carbonate stream in the one or more carboxylation reactors, the ethylene carbonate stream is then converted to a first ethylene glycol stream in one or more hydrolysis reactors.

However, in a preferred embodiment of the process of the present invention, prior to being supplied to the one or more hydrolysis reactors, the ethylene carbonate stream is subjected to a carbon dioxide separation step in a carbon dioxide separation vessel. In this step, carbon dioxide is removed from the stream comprising the ethylene carbonate and the carbon dioxide may then be recycled to the carbon dioxide stream to be supplied to the carboxylation reactor.

The one or more hydrolysis reactors may be any suitable reactor type. Preferably, the hydrolysis reactors are baffled reactors. If there is more than one hydrolysis reactor it is preferred that the hydrolysis reactors are connected in series.

In one embodiment of the invention, at least one of the one or more hydrolysis reactors is a baffled reactor, wherein the baffled reactor has at least 3, preferably at least 4 compartments, the compartments are formed by internal baffles and the internal baffles provide a sinuous route for reaction fluid through the reactor. Optionally, steam is injected into the baffled reactor.

Carbon dioxide may be produced in the one or more hydrolysis reactors and is preferably separated from the product stream as it leaves the one or more hydrolysis reactors and recycled to the carbon dioxide stream to be supplied to the carboxylation reactor.

The temperature in the one or more hydrolysis reactors is typically from 100 to 200° C., preferably from 100 to 180° C. The pressure in the one or more hydrolysis reactors is typically from 0.1 to 3 MPa.

The first ethylene glycol stream is supplied to a dehydrator. Water is recovered from the dehydrator. Some of the water may be recycled, but some of the water is removed as a waste water stream. Preferably all of the water is removed as a waste water stream.

The dehydrator is preferably one or more columns, including at least one vacuum column, preferably operating at a pressure of less than 0.05 MPa, more preferably less than 0.025 MPa and most preferably about 0.0125 MPa.

The dehydrated ethylene glycol stream is then purified to remove impurities and provide a purified ethylene glycol product stream. The one or more homogeneous catalysts are separated in the catalyst separation section to provide a catalyst recycle stream. The catalyst recycle stream is then supplied to the carboxylation reactor.

The first ethylene glycol stream comprises inorganic chloride contaminants. These inorganic contaminants arise because the moderator in the ethylene oxide reactor produces organic chloride contaminants that are supplied to the ethylene oxide absorber, and these contaminants are consequently supplied to the carboxylation and hydrolysis reactors. The organic chloride contaminants react with the carboxylation and/or hydrolysis catalysts, providing inorganic chloride contaminants in the first ethylene glycol stream.

The present inventors have found that the inorganic chloride contaminants can be converted to 2-chloroethanol by reaction with ethylene oxide in the one or more dehydration columns. This 2-chloroethanol is removed in the waste water stream. Reducing the inorganic chloride contaminants in this way reduces the requirement for a catalyst bleed.

In conventional processes typically there is no ethylene oxide in the one or more dehydration columns. Therefore, to carry out the process of the invention, the skilled person must ensure that there is sufficient ethylene oxide in the one or more dehydration columns to convert the inorganic chloride contaminants. In a first embodiment of the invention, the skilled person ensures that the conversion in step (iv) of the process is not complete so that not all the ethylene carbonate in the ethylene carbonate stream is converted to ethylene glycol, and the first ethylene glycol stream comprises ethylene carbonate. Preferably there is up to 8000 ppm of ethylene carbonate in the first ethylene glycol stream, more preferably up to 5000 ppm. The ethylene carbonate in the first ethylene glycol stream will be at least partially converted to ethylene oxide in the one or more dehydration columns. This ethylene oxide can then react with the inorganic chloride contaminants.

In a second embodiment of the invention, the skilled person can add ethylene carbonate to the one or more dehydration columns. This ethylene carbonate will be at least partially converted to ethylene oxide in the one or more dehydration columns and can then react with the inorganic chloride contaminants. Preferably up to 8000 ppm of ethylene carbonate is added to the one or more dehydration columns, more preferably up to 5000 ppm. Preferably the ethylene carbonate is added into the first ethylene glycol stream before it is supplied to the one or more dehydration columns. The ethylene carbonate is preferably supplied in the form of a process stream that comprises ethylene carbonate. For example, the process stream could further comprise ethylene glycol. The process stream could be a bleed from the carboxylation reactor.

When ethylene carbonate is converted into ethylene oxide in the one or more dehydration columns as in the first and second embodiments of this invention, carbon dioxide will be produced. Such production of carbon dioxide may mean that there is a greater vacuum requirement to maintain the required pressure in the one or more dehydration columns.

In a third embodiment of the invention, the skilled person can add ethylene oxide to the one or more dehydration columns. This ethylene oxide can then react with the inorganic chloride contaminants. Preferably the ethylene oxide is added into the first ethylene glycol stream before it is supplied to the one or more dehydration columns. The ethylene oxide is preferably supplied in the form of a process stream that comprises ethylene oxide. For example, the process stream could further comprise water. The process stream could be a portion of the concentrated ethylene oxide stream from the top of the ethylene oxide stripper.

FIG. 1 shows a possible process of the present invention.

In the process for the production of an ethylene glycol from ethylene, an aqueous ethylene oxide stream (1) from the ethylene to ethylene oxide part of the process, provided via an inlet (1a), is mixed with water (2), a catalyst stream (15) and carbon dioxide (3) before being supplied to the first of the one or more carboxylation reactors (4). These carboxylation reactors have liquid recycles (5a and 5b). The ethylene carbonate stream (6) is passed to a carbon dioxide separation vessel (7). Excess carbon dioxide is recycled via a recycle stream (8). The ethylene carbonate stream is then fed into the first of the one or more hydrolysis reactors (9), where it is converted to a first ethylene glycol stream (10). Carbon dioxide produced in a hydrolysis reactor is recycled via recycle stream (8). The first ethylene glycol stream (10) is then dehydrated in a dehydrator (11) to provide a dehydrated ethylene glycol stream (12) and a waste water stream (17). The dehydrated ethylene glycol stream (12) is purified in one or more glycol distillation columns (13) to provide a purified ethylene glycol product stream (14) and a catalyst recycle stream (15).

The first ethylene glycol stream (10) comprises inorganic chloride contaminants. In a first embodiment of the invention, the hydrolysis in the hydrolysis reactors (9) is incomplete such the first ethylene glycol stream (10) comprises ethylene carbonate. This ethylene carbonate is at least partially converted to ethylene oxide in the dehydrator (11). The ethylene oxide reacts with the inorganic chloride contaminants in the dehydrator (11), providing 2-chloroethanol. The 2-chloroethanol is removed from the system via the waste water stream (17).

In alternative embodiments, ethylene carbonate or ethylene oxide can be supplied (16) into the first ethylene glycol stream (10).

A conventional process would use a catalyst bleed (18) to remove inorganic chloride contaminants from the system. The need for such a bleed is reduced and potentially removed by the process of the invention.

It will be clear to the skilled person, that as a schematic diagram this figure does not show all inputs and recycle streams that may be present in the process.

EXAMPLES

The invention is further illustrated by means of the following non-limiting examples.

Experiments were carried out using apparatus substantially as shown in FIG. 1. The reaction in the hydrolysis reactors (9)

was controlled such that the first ethylene glycol stream (10) contained ethylene carbonate at the levels given in Table 1 below. Table 1 also shows the level of inorganic chloride contaminants in the first ethylene glycol stream, the total feed to the dehydrator (11), the waste water flow (17) and the amount of chloroethanol in the waste water stream (17):

TABLE 1

|  | Ethylene carbonate in feed (ppm) | Chloride ions in feed (ppm) | Total feed (g/h) | Waste water flow (g/h) | Chloroethanol in waste water (ppm) |
| --- | --- | --- | --- | --- | --- |
| Example 1 | 900 | 943 | 115 | 12.6 | 14.9 |
| Example 2 | 460 | 1491 | 125 | 11.4 | 8.4 |
| Example 3 | 2990 | 1608 | 123 | 12.2 | 49.8 |

In these examples the ethylene carbonate reacted in the dehydrator to produce ethylene oxide, which further reacted with chloride ions, leading to chloroethanol in the waste water.

This experimental data was used to prepare a prediction of how chloroethanol in waste water varies as a function of the ethylene carbonate level in the first ethylene glycol stream. FIG. 2 shows the amount of chloroethanol in waste water versus the amount of ethylene carbonate in the feed for conditions of 1500 ppm chloride ions in the feed, 145 mmol/kg of iodide ions in the feed, a feed flow of 123 g/h and a waste water flow of 12 g/h. The amount of chloroethanol in the waste water is directly proportional to the amount of ethylene carbonate in the feed.

What is claimed is:

1. A process for the production of ethylene glycol from ethylene, said process comprising the steps of:
   i) converting ethylene in the presence of oxygen, an epoxidation catalyst and a moderator to ethylene oxide in an ethylene oxide reactor;
   ii) absorbing the ethylene oxide in an aqueous absorbent and then stripping said absorbent to provide an aqueous ethylene oxide stream;
   iii) converting the aqueous ethylene oxide stream in the presence of one or more catalysts and carbon dioxide to an ethylene carbonate stream in one or more carboxylation reactors;
   iv) converting the ethylene carbonate stream in the presence of one or more catalysts to a first ethylene glycol stream in one or more hydrolysis reactors;
   v) removing water from the first ethylene glycol stream to form a dehydrated ethylene glycol stream and a waste water stream in one or more dehydration columns;
   vi) purifying the dehydrated ethylene glycol stream in one or more glycol distillation columns to form a purified ethylene glycol product stream and a catalyst recycle stream;
   wherein the first ethylene glycol stream comprises inorganic chloride contaminants and wherein the process comprises the additional steps of vii) converting the inorganic chloride contaminants to 2-chloroethanol by reaction with ethylene oxide in the one or more dehydration columns; and
   viii) removing 2-chloroethanol in the waste water stream.

2. A process according to claim 1, wherein conversion in step (iv) of the process is not complete so that not all the ethylene carbonate in the ethylene carbonate stream is converted to ethylene glycol, and the first ethylene glycol stream comprises ethylene carbonate.

3. A process according to claim 2, wherein there is up to 8000 ppm of ethylene carbonate in the first ethylene glycol stream.

4. A process according to claim 1, comprising an additional step of adding ethylene carbonate to the one or more dehydration columns.

5. A process according to claim 4, wherein up to 8000 ppm of ethylene carbonate is added to the one or more dehydration columns.

6. A process according to claim 4, wherein the ethylene carbonate is added into the first ethylene glycol stream before it is supplied to the one or more dehydration columns.

7. A process according to claim 4, wherein the ethylene carbonate is supplied in the form of a process stream that comprises ethylene carbonate.

8. A process according to claim 1, comprising an additional step of adding ethylene oxide to the one or more dehydration columns.

9. A process according to claim 8, wherein the ethylene oxide is added into the first ethylene glycol stream before it is supplied to the one or more dehydration columns.

10. A process according to claim 8, wherein the ethylene oxide is supplied in the form of process stream that comprises ethylene oxide.

* * * * *